(12) United States Patent
Yan et al.

(10) Patent No.: US 11,464,570 B2
(45) Date of Patent: Oct. 11, 2022

(54) SYSTEM AND METHOD FOR PLANNING AND PERFORMING AN INTERVENTIONAL PROCEDURE BASED ON THE SPATIAL RELATIONSHIPS BETWEEN IDENTIFIED POINTS

(71) Applicants: KONINKLIJKE PHILIPS N.V., Eindhoven (NL); THE UNITED STATES OF AMERICA, as represented by the Secretary, Department of Health and Human Services, Bethesda, MD (US)

(72) Inventors: Pingkun Yan, Gaithersburg, MD (US); Peter A Pinto, Bethesda, MD (US); Jochen Kruecker, Andover, MA (US); Bradford Johns Wood, Bethesda, MD (US)

(73) Assignees: KONINKLUKE PHILIPS N.V., Endhoven (NL); THE UNITED STATES of AMERICA, as Represented by the Secreatary, Dept. of Health and Human Services, Bethesda, MD (US)

( * ) Notice: Subject to any disclaimer, the term of this patent is extended or adjusted under 35 U.S.C. 154(b) by 780 days.

(21) Appl. No.: 16/328,295

(22) PCT Filed: Sep. 29, 2017

(86) PCT No.: PCT/EP2017/074741
§ 371 (c)(1),
(2) Date: Feb. 26, 2019

(87) PCT Pub. No.: WO2018/060404
PCT Pub. Date: Apr. 5, 2018

(65) Prior Publication Data
US 2019/0209244 A1 Jul. 11, 2019

Related U.S. Application Data

(60) Provisional application No. 62/401,329, filed on Sep. 29, 2016.

(51) Int. Cl.
*A61B 34/10* (2016.01)
*A61B 10/00* (2006.01)
(Continued)

(52) U.S. Cl.
CPC .............. *A61B 34/10* (2016.02); *A61B 10/00* (2013.01); *G06T 7/0012* (2013.01); *G16H 30/20* (2018.01);
(Continued)

(58) Field of Classification Search
CPC ......... A61B 34/20; A61B 34/10; A61B 34/25; A61B 34/107; A61B 10/00;
(Continued)

(56) References Cited

U.S. PATENT DOCUMENTS 10,255,723 B2 4/2019 Thomas
10,321,898 B2 6/2019 Weingarten
(Continued)

FOREIGN PATENT DOCUMENTS

EP 2777564 A1 9/2014

OTHER PUBLICATIONS

Varinak Onkoloji, "DICOM Viewer-Medical Image Manipulation", youtube Apr. 10, 2015, p. 2 pp. https://www.youtube.com/watch?v=J8OusujklNk.

*Primary Examiner* — Vu Le
*Assistant Examiner* — Julius Chai
(74) *Attorney, Agent, or Firm* — Sherry Austin

(57) ABSTRACT

A system and method for planning and performing an interventional procedure based on the spatial relationships
(Continued)

between identified points. The system includes a storage device (102) having an image (104) which includes a plurality of targets (107). A spatial determination device (114) is configured to determine distances and/or orientation between each of the targets. The system is configured to compare the distances and generate a warning signal if at least one of the distances is less than a minimum threshold (128). An image generation device (116) is configured to generate a graphical representation for display to the user which shows the spatial information between a selected target with respect to the other targets. A planning device (126) is configured to modify or consolidate targets automatically or based on a user's input in order to more effectively plan or execute an interventional procedure.

15 Claims, 4 Drawing Sheets

(51) Int. Cl.
G16H 30/20 (2018.01)
G06T 7/00 (2017.01)
A61B 8/08 (2006.01)
A61B 90/00 (2016.01)
A61B 10/02 (2006.01)

(52) U.S. Cl.
CPC ......... *A61B 8/5238* (2013.01); *A61B 10/0241* (2013.01); *A61B 2034/107* (2016.02); *A61B 2090/364* (2016.02)

(58) Field of Classification Search
CPC .......... A61B 10/0241; A61B 2090/364; A61B 8/5238; G16H 30/30; G06T 7/0012
See application file for complete search history.

(56) References Cited

U.S. PATENT DOCUMENTS

| | | | |
|---|---|---|---|
| 10,543,050 B2 | 1/2020 | Itkowitz | |
| 10,588,541 B2 | 3/2020 | Lorraine | |
| 10,980,508 B2 | 4/2021 | Xu | |
| 11,051,902 B2 | 7/2021 | Kruecker | |
| 2006/0079771 A1 | 4/2006 | Nir | |
| 2008/0161687 A1 | 7/2008 | Suri et al. | |
| 2009/0048515 A1 | 2/2009 | Suri et al. | |
| 2009/0118640 A1 | 5/2009 | Miller et al. | |
| 2009/0171184 A1 | 7/2009 | Jenkins et al. | |
| 2010/0284588 A1* | 11/2010 | Valadez | G06T 7/0012 382/128 |
| 2014/0303662 A1 | 10/2014 | Aoyagi | |
| 2015/0097868 A1 | 4/2015 | Banerjee et al. | |
| 2016/0000414 A1 | 1/2016 | Brown et al. | |

* cited by examiner

| Targets | T1 | T2 | ... | TN |
|---|---|---|---|---|
| T1 | 0.0 | $d_{12}$ | ... | $d_{1N}$ |
| T2 | $d_{21}$ | 0.0 | ... | $d_{2N}$ |
| ... | ... | ... | ... | ... |
| TN | $d_{N1}$ | $d_{N2}$ | ... | 0.0 |

| Distance range | # targets | Target tags |
|---|---|---|
| $d_0$ | m | RBL, RMM, old T1, ... |
| $d_1$ | n | RBM, RML, ... |
| $d_2$ | l | RAL, old T2, ... |

122

SYSTEM AND METHOD FOR PLANNING AND PERFORMING AN INTERVENTIONAL PROCEDURE BASED ON THE SPATIAL RELATIONSHIPS BETWEEN IDENTIFIED POINTS

CROSS-REFERENCE TO PRIOR APPLICATIONS

This application is the U.S. National Phase application under 35 U.S.C. § 371 of International Application Serial No. PCT/EP2017/074741, filed on Sep. 29, 2017, which claims the benefit of U.S. Patent Application No. 62/401,329, filed on Sep. 29, 2016. This application is hereby incorporated by reference herein.

This invention was made in the performance of a Cooperative Research and Development Agreement with the United States Public Health Service (CRADA No. NCI-NIHCC-01864). The Government of the United States has certain rights in the invention.

BACKGROUND

Technical Field

This disclosure relates to systems and methods for planning and performing interventional procedures and, in particular, systems and methods for planning and performing interventional procedures based on the spatial relationships between identified points.

Description of the Related Art

Numerous image-guided interventional procedures, such as image-guided targeted biopsy or localized therapy procedures, include imaging having a plurality of identified points. For example, in order to improve the visualization and guidance provided to a user during an interventional procedure, systems have been developed which map prior biopsy or treatment locations on imaging for new procedures to permit monitoring of these points during the performance of the new procedure. For instance, a system for planning and performing a repeat interventional procedure has been developed which is configured to register current targets in a reference image for a first interventional procedure to a guidance image acquired from a different imaging modality for improved visualization and guidance during the performance of the interventional procedure.

These image-guided systems include a plurality of identified points or "targets" in the imaging in order to provide increased information to the user performing the interventional procedure. However, the information provided by these systems is often only of limited value to the user. For example, the mapping of prior biopsies or local treatments into new procedures may lead to a large number of potential biopsy targets and it is difficult to determine which targets to focus on during the interventional procedure. Furthermore, the mapped images present the targets as single points when lesions are masses with volumes. Therefore, several nearby target points may all be part of the same lesion and it is advantageous to biopsy or treat points from the same lesion together and not independently. However, in these prior image guided systems, it is difficult to assess which of the numerous biopsy and/or treatment targets in the mapped images, such as related or spatially close points, may be consolidated without losing diagnostic information or treatment value.

It would be advantageous to provide a system for an image-guided interventional procedure which provides the practitioner with spatial relationships between the plurality of identified points, such as biopsy targets, to provide the practitioner with an improved understanding of the distribution of the targets. The provision of the spatial information between the targets increases the usefulness of the information provided to the practitioner in an image guided interventional procedure and improves the practitioner's ability to effectively plan and execute the interventional procedure.

SUMMARY

In accordance with the present principles, a system for planning and performing an interventional procedure includes a storage device configured to store an image which includes a plurality of targets for the interventional procedure. The system further includes a spatial determination device configured to determine distances between each of the targets. A planning device is configured to compare the distances between each of the targets and generate a signal if at least one of the distances is less than a minimum threshold. An image generation device is configured to generate a graphical representation on a display device which shows distances between a selected target with respect to other targets of the plurality of targets.

In another embodiment, a system for planning and performing a repeat interventional procedure based on spatial relationships includes a storage device configured to store an enhanced planning image which includes at least one prior biopsy location and/or at least one prior treatment location from a prior image mapped to a current planning image that includes at least one current target area for a current interventional procedure. A spatial determination device is configured to determine a distance between each of the at least one prior biopsy location and/or at least one prior treatment location and the at least one current target area. An image generation device is configured to generate a graphical representation on a display device which shows distances between each of the at least one prior biopsy location and/or at least one prior treatment location and the at least one current target area.

In another embodiment, a method for planning and performing an interventional procedure includes the step of obtaining an image which includes a plurality of targets for the interventional procedure from a storage device. The method further includes the step of determining distances between the plurality of targets. A signal is generated if at least one of the distances is less than a minimum threshold. A graphical representation is generated which shows distances between a selected target with respect to other targets of the plurality of targets.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
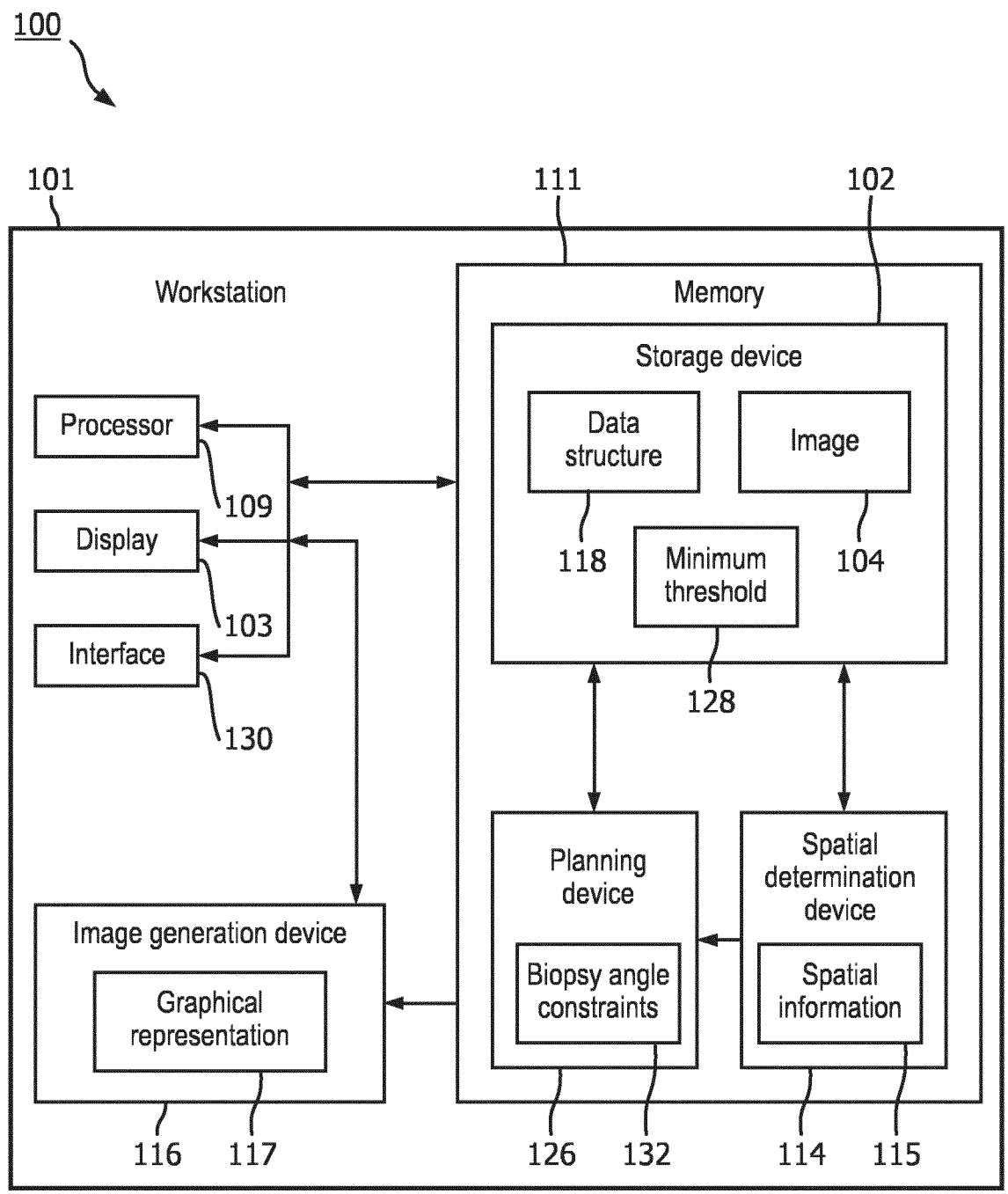
FIG. 1 is a block/flow diagram showing a system for planning and performing an interventional procedure based on spatial relationships in accordance with one illustrative embodiment.

In accordance with the present principles, a system for planning and performing an interventional procedure based on the spatial relationships of identified points is provided. The system presents the distance and/or orientation between identified points in an image which contains a plurality of identified points to enable the user to clearly determine biopsy or treatment targets that may be consolidated or modified without losing diagnostic information or therapeutic value. The presentation of the spatial information between identified points in an image also enables the user to account for inaccuracies in the navigation system or the target mapping process. The system also permits the user to plan and execute an interventional procedure, such as a biopsy, with a minimal number of biopsy sites.

The system also provides improved monitoring of cancer progression, a higher treatment efficacy and lower morbidity by analyzing and displaying the spatial relationships of a plurality of identified points in the image and permitting the determination, either automatically or interactively, concerning which points may be targeted or modified.

It should be understood that the present invention will be described in terms of medical systems. However, the teachings of the present invention are much broader and in some embodiments, the present principles are employed in quantitatively evaluating complex biological or mechanical systems. Furthermore, the present principles are applicable to internal evaluation procedures of biological systems in all areas of the body such as the lungs, liver, brain, uterus, gastro-intestinal tract, excretory organs, blood vessels, and any other solid organ tissue, tumor tissue and homogenously or heterogeneously enhancing structures of the body. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Similarly, it will be appreciated that various processes may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

In accordance with the present principles, a system for planning and performing an interventional procedure based on spatial relationships between points identified in the imaging is provided. Referring now to the drawings in which like numerals represent the same or similar elements and initially to FIG. 1, a system 100 includes a storage device 102 that is configured to store an image 104 of a region of a subject which includes a plurality of identified points 107 for an image-guided interventional procedure. For example, in one embodiment, the image 104 is an enhanced planning image that includes at least one prior biopsy location and/or at least one prior treatment location from a prior image that is mapped to a current planning image which includes at least one current target area for a current interventional procedure.

The enhanced planning image may be generated by a mapping device that receives a planning image of the region of the subject, such as an MRI image, computed tomography ("CT") image, a positron emission tomography ("PET") image, ultrasound image or an image from other imaging modalities known in the art. The planning image includes at least one current target area for a planned interventional procedure. The mapping device may include a registration device that is configured to spatially register each target area in the planning image to a prior image which includes at least one prior biopsy location and/or at least one prior treatment location indicated in the image in the prior image coordinate space. After the transformation is performed by the registration device, the registration device is configured to apply the transformation to the coordinates of the target areas in the planning image or the locations of the prior biopsy locations and treatment locations in the prior image so that their locations are in the same coordinate space in order to generate the enhanced planning image having each of these points in a single coordinate system. While the image is generally disclosed illustratively to include current and prior targets for current and past interventional procedures, in other embodiments, the image 104 may be for a single study wherein all of the identified points 107 are new targets.

The system also includes a spatial determination device 114 that is configured to analyze the image 104 of the subject and determine a distance between each of the identified points/targets 107, such as the prior biopsy locations and prior treatment locations to the current targets. While the identified points are generally referred to herein as "targets", the points may be other areas of interest in the image of the subject as generally known in the art.

The distance determination may be made by the spatial determination device 114 by analyzing the plurality of points 107 in the common coordinate system of the image 104 and quantifying the amount of space between the points in the common coordinate system. In a preferred embodiment, the spatial determination device 114 is also configured to determine an orientation of the prior biopsy locations and prior treatment locations to the current target areas in the image 104. The orientation may be determined in the common coordinate system of the image 104 by numerous methods known in the art. The distance and orientation of the identified points is referred to herein as the "Spatial Information".

Figures 2, 3:
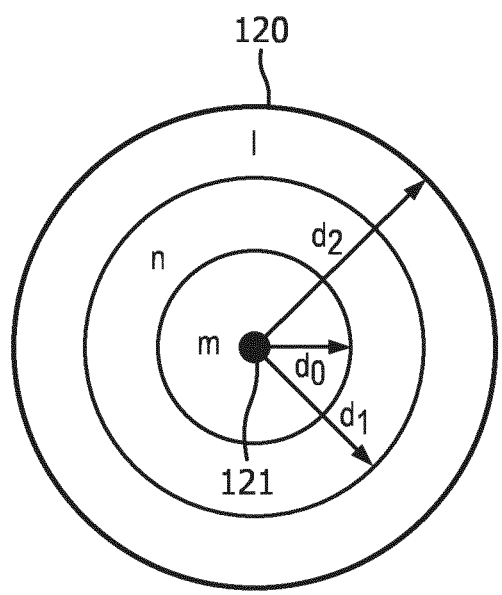
FIG. 2 shows a data table generated by the system in accordance with one illustrative embodiment.
FIG. 3 shows a graph generated by the system in accordance with one illustrative embodiment.

The spatial determination device 114 is configured to record the Spatial Information in one or more data structures 118 that are generally known in the art. For example, as shown in FIG. 2, the spatial determination device 114 may be configured to record the Spatial Information in a data table 119 which includes targets $T_1$-$T_N$ and distances for each entry indicating the distance between the two targets. For instance, the data table 119 shown in FIG. 2 indicates that target $T_2$ is a distance of $d_{21}$ apart from target $T_1$. The spatial determination device 114 may be configured to send the data structure 118, such as the data table 119, to the storage device 102 in order to store the data structure so that the Spatial Information may be retrieved at a later time. While the data table shown in FIG. 2 solely shows Spatial Information comprising distance, the relative orientation of the targets may be recorded in a data table 119 in a similar manner, either separately or in combination with the distance data.

The system 100 also includes a planning device 126. The planning device 126 is configured to receive the Spatial Information 115 from the spatial determination device 114 and analyze the spatial information. In a preferred embodiment, the planning device 126 is configured to automatically compare the distances between targets and determine if any targets are too close. In one embodiment, the planning device 126 is configured to receive a minimum threshold 128 stored in the storage device 102. The minimum threshold 128 is the minimum distance which targets identified in the image should be apart from each other. The minimum threshold 128 may be related to the size of clinically significant target structures and to the accuracy in obtaining a biopsy core from a planned location. For example, in one embodiment, the minimum threshold 128 for prostate Magnetic Resonance Imaging-Ultrasound fusion biopsies may be 3 mm. The minimum threshold 128 may be predetermined or determined by the user during the procedure. The minimum threshold 128 may also be adjusted by the user during the procedure.

The planning device 126 is configured to automatically review the determined distances between the points/targets 107 and determine if any of the distances are smaller than the minimum threshold 128. If the planning device 126 determines that the determined spatial distances between any pair of targets is smaller than the minimum threshold 128, the planning device may be configured to generate a warning message to alert the user to this issue.

The system 100 preferably includes an image generation device 116. In one embodiment, the planning device 126 is configured to provide a signal to the image generation device 116 which is configured to respond to the signal by generating a graphical warning on the display 103 concerning the target pairs being smaller than the minimum threshold. In alternative embodiments, the planning device 126 may be configured to generate signals for the system to produce other visual, audible or tactile warnings. The planning device 126 may also be configured to evaluate the orientations between identified points and provide similar signals for generation of a warning based on the determined orientations.

In a preferred embodiment, the system 100 may include a workstation 101 from which the procedure is supervised and/or managed. The workstation 101 preferably includes one or more processors 109 and memory 111 for storing programs and applications. In one embodiment, the storage device 102 may be integrated within the memory 111 of the system. The display 103 permits a user to view images and interact with the workstation 101. The system 100 may further include an interface 130 which may feature a keyboard, mouse, a joystick, a haptic device, or any other peripheral or control to permit user feedback from and interaction with the workstation 101.

The system 100 described in FIG. 1 is configured to display the image 104 which includes multiple points or targets 107 such as current target areas and previous target locations and biopsy locations as well as the Spatial Information 115. In a preferred embodiment, the system 100 may be configured to present the image 104 on the display and permit the user to browse the targets and interactively select a target using the interface 130. For example, a user may use the interface 130 to choose a highly suspicious current target in the image 104. The Spatial Information that is determined and displayed by the system then permits the user to determine if an old target is in close proximity to the current target in order to more effectively plan and execute the interventional procedure.

The image generation device 116 is configured to receive the Spatial Information 115 determined by the spatial determination device 114 and generate a graphical representation 117 of the distance and/or orientation between each of the prior biopsy and treatment locations and a current target area selected by the user. The image generation device 116 is configured to send the graphical representation 117 to the display 103 to permit the user to view the graphical representation in order to improve the planning and execution of the interventional procedure.

In one embodiment, the image generation device 116 is configured to generate a graph 120 concerning the spatial distance between a selected target and other targets. For example, in the embodiment shown in FIG. 3, the graph 120 includes a white circular symbol 121 in the center which identifies the selected target. The graph also includes distance ranges $d_0$, $d_1$, $d_2$. The graph 120 shown in FIG. 3 indicates that the m targets are less than $d_0$ away, the n targets are less than $d_1$ away and the l targets are less than $d_2$ away. The graph 120 may also include information indicating the relative orientation of the targets.

In another embodiment, the image generation device 116 may be configured to generate a table 122 concerning the Spatial Information. For example, in the embodiment shown in FIG. 4, a table 122 generated by the image generation device includes a distance range, the number of targets and target tags. The target tags provides more detailed information such as the tags of nearby targets. This permits the user to immediately know which targets are close to a selected target. The image generation device 116 may be configured to generate the graphical representation 117, such as the table 122, in combination with other graphical representations in order to improve the clarity of the displayed images.

Figures 4, 5:
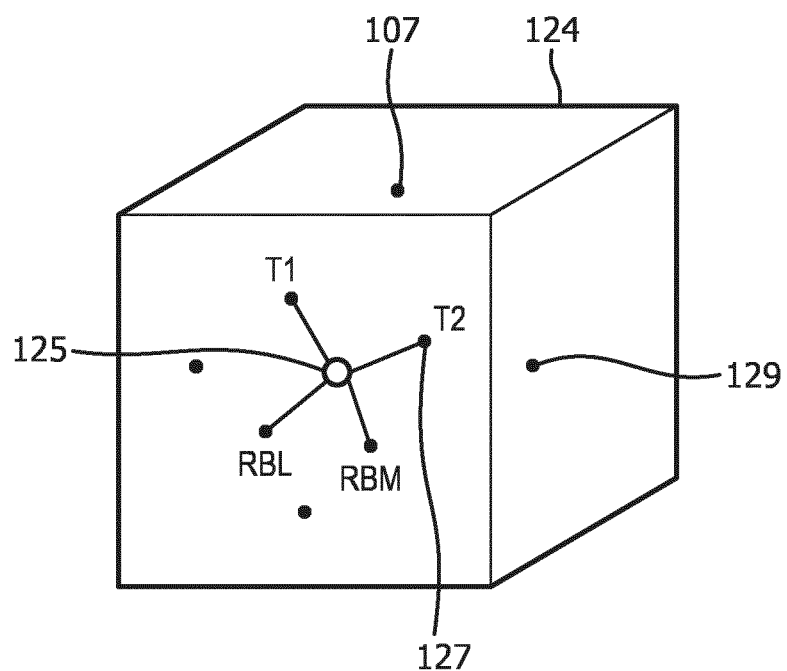
FIG. 4 shows a table generated by the system in accordance with one illustrative embodiment.
FIG. 5 shows a three-dimensional image generated by the system in accordance with one illustrative embodiment.

The image generation device 116 may also be configured to generate a three-dimensional image 124 depicting the determined spatial relationship. For example, in the embodiment shown in FIG. 5, a three-dimensional image 124 includes targets $T_1$, $T_2$ and tags of targets RBL, RBM. The image shows the orientation and distance of the targets with respect to each other. The selected target is indicated with a circular symbol 125 having a dark outer periphery and a white interior. Targets may be color coded depending on their distances to the selected target. For example, the three-dimensional image 124 in FIG. 5 shows the targets within a single range wherein targets within a particular range are denoted with a white circular symbol 127 while targets outside the range are denoted with a dark circular symbol 129. While FIG. 5 shows only one range, the three-dimensional representation 124 may indicate the targets with respect to multiple ranges based on additional color coding. Furthermore, additional target tags may be displayed in the three-dimensional image.

The user may easily view the Spatial Information in the image generated by the image generation device 116 and clearly understand the distribution of the targets 107. The user may then manually input commands for the planning device 126 using the interface 130. The planning device 126 is configured to receive the commands from the user and consolidate or modify the targets 107 in the image 104 in accordance with the commands. For example, the user may view the graphical representation 117 generated by the image generation device 116 on the display 103 and manually eliminate targets in the image 104 using the planning device 126, such as targets that are very close to each other. Alternatively, the user may combine multiple targets into a reduced number of targets in the image 104. The user may also modify the location of the targets 107 based on the Spatial Information.

The presentation of the Spatial Information concerning the plurality of targets permits the user to better assess the pertinence of a particular target such as by evaluating the distance of a current target from an old biopsy or treatment site. The presentation of the Spatial Information may also permit the user to identify targets which may be on the same lesion or which have been previously biopsied or treated in order to improve the planning of the current interventional procedure.

In another embodiment, the planning device 126 may be configured to receive the image 104 and the Spatial Information 115 and automatically determine points to consolidate or modify based on the Spatial Information without input from the user. In this embodiment, the planning device 126 may utilize pre-determined instructions concerning modification and consolidation of the points 107 based on the Spatial Information 115. The pre-determined instructions may utilize the minimum threshold 128 and other data to distinguish the targets.

In a preferred embodiment the planning device 126 is configured to utilize predetermined biopsy angle constraints 132 to determine whether to modify a target 107 in the image 104. For example, a biopsy core is typically cylindrical and physical constraints in the angulation of the biopsy gun permit only a limited range of angles in which the biopsy core may be obtained. Therefore, two or more closely spaced targets may only be covered in a single biopsy core if they are aligned within an acceptable angle that is within the physical constraints of the biopsy device. The planning device 126 may be configured to analyze the biopsy angle constraints 132 and automatically delete points that are not able to be accessed in a single biopsy core and consolidate points that are able to be accessed in a single biopsy core. Alternatively, the system 100 may be configured to present the information concerning biopsy point constraints 132 on the display 103 so that the user may manually determine the targets that should be modified by inputting commands for the planning device 126 into the interface 130.

Furthermore, the planning device 126 may be configured to distinguish between systematic targets and image-based targets. Systemic targets are generated by a system typically in compliance with a standard planning procedure. For example, systemic targets may be a result of a sextant biopsy in the prostate which generates targets having a uniform distribution throughout the organ of the subject. In contrast, image-based targets are regions that have been identified based on suspicious findings in an image-based diagnostic or interventional procedure. Since the specific locations of systematic targets do not directly reflect their diagnostic value, the planning device 126 may be configured to modify these systematic points with greater flexibility than an image-based target.

Figure 6:
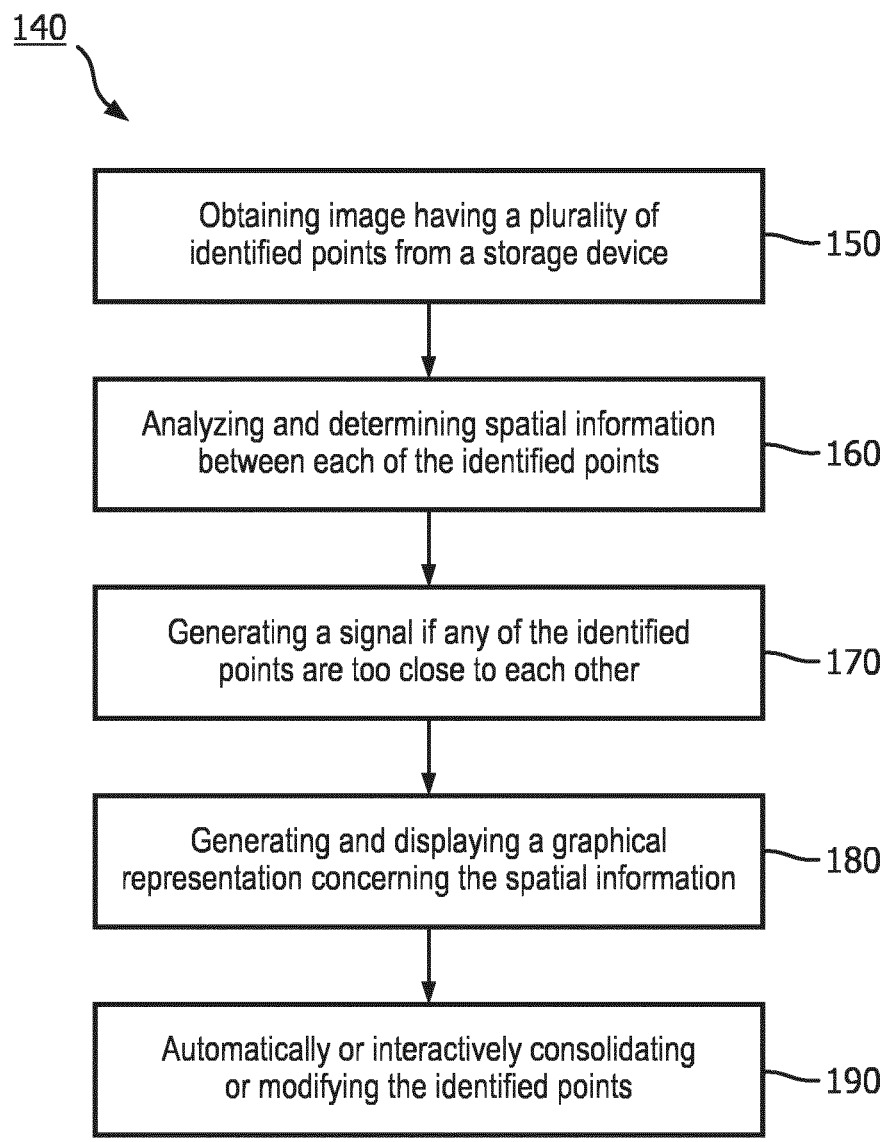
FIG. 6 is a flow diagram showing a method for planning and performing an interventional procedure in accordance with one illustrative embodiment.

Referring to FIG. 6, a method 140 for planning and performing an interventional procedure based on the spatial relationships between identified points is illustratively shown in accordance with the present principles. In block 150, an image which includes a plurality of identified points is obtained from a storage device. In block 160, the image is analyzed and Spatial Information is determined between each of the identified points, such as the distance and/or orientation between the points. In block 170, a warning signal is generated to the user if any of the identified points are too close to each other. For example, if the distance between identified points is less than a minimum threshold, a warning signal such as a visual, audible or tactile warning is generated to the user.

In block 180, a graphical representation of the Spatial Information is generated and provided on a display for the user for a target area selected by the user. In block 190, one or more of the identified points in the image may be automatically or interactively consolidated, modified or deleted.

It is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for the system and method for planning and performing an interventional procedure in a subject (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for planning and performing an interventional procedure, comprising:
   a storage device configured to store an image which includes a plurality of targets for the interventional procedure;
   a spatial determination device configured to determine distances between each of the targets;
   a planning device configured to compare the distances between each of the targets and generate a signal if at least one of the distances is less than a minimum threshold; and
   an image generation device configured to generate on a display device a graphical representation which shows distances between a selected target with respect to other targets of the plurality of targets.

2. The system as recited in claim 1, wherein the spatial determination device is also configured to determine orientations between the plurality of targets.

3. The system as recited in claim 2, wherein the spatial determination device is configured to record the distances and/or orientations between the plurality of targets as a data structure.

4. The system as recited in claim 3, wherein the spatial determination device is configured to record the distances and/or orientations as a table.

5. The system as recited in claim 1, wherein the system is configured to generate a graphical warning on the display device in response to the signal that is generated if at least one of the distances is less than the minimum threshold.

6. The system as recited in claim 2, wherein the planning device is configured to automatically consolidate or modify the plurality of targets based on the distances and/or orientations.

7. The system as recited in claim 6, wherein the planning device is configured to automatically consolidate or modify the plurality of targets based on determined angles of targets by further taking into account physical constraints of an interventional device to perform at the determined angles.

8. The system as recited in claim 1, wherein the system further includes an input device for a user and the planning device is configured to consolidate or modify the plurality of targets based on commands input by the user into the input device.

9. The system as recited in claim 1, wherein the image generation device is configured to generate a graphical representation comprising at least one of a graph, table or 3D image.

10. A system for planning and performing a repeat interventional procedure, comprising:
    a storage device configured to store an enhanced planning image which includes at least one prior biopsy location and/or at least one prior treatment location from a prior image mapped to a current planning image that includes at least one current target area for a current interventional procedure;
    a spatial determination device configured to determine a distance between each of the at least one prior biopsy location and/or at least one prior treatment location and the at least one current target area;
    an image generation device configured to generate on a display device a graphical representation which shows distances between each of the at least one prior biopsy location and/or at least one prior treatment location and the at least one current target area;
    wherein the spatial determination device is also configured to determine orientations between each of the at least one prior biopsy location and/or at least one prior treatment location and the at least one current target area; and
    wherein the system further includes a planning device configured to compare the distances between each of the at least one prior biopsy location and/or at least one prior treatment location and the at least one current target area and generate a signal if at least one of the distances is less than a minimum threshold.

11. The system as recited in claim 10, wherein the planning device is configured to automatically consolidate or modify the at least one prior biopsy location and/or at least one prior treatment location and the at least one current target based on the distances and/or orientations.

12. The system as recited in claim 10, wherein the system further includes an input device for a user and the planning device is configured to consolidate or modify the at least one prior biopsy location and/or at least one prior treatment location and the at least one current target based on commands input by the user into the input device.

13. A method for planning and performing an interventional procedure, comprising:
    obtaining an image which includes a plurality of targets for the interventional procedure from a storage device;
    determining distances between the plurality of targets;
    generating a signal if at least one of the distances is less than a minimum threshold; and
    generating a graphical representation which shows distances between a selected target with respect to other targets of the plurality of targets.

14. The method as recited in claim 13, further comprising the step of determining orientations between the plurality of targets.

15. The method as recited in claim 14, further comprising the step of recording the distances and orientations as a data structure.

* * * * *